United States Patent [19]
Breitling et al.

[11] Patent Number: 5,849,500
[45] Date of Patent: Dec. 15, 1998

[54] PHAGEMID FOR ANTIBODY SCREENING

[75] Inventors: Frank Breitling, Heidelberg; Melvyn Little, Neckargemünd; Stefan Dübel, Heidelberg; Michael Braunagel; Iris Klewinghaus, both of Mannheim, all of Germany

[73] Assignee: Deutsches Krebsforschungszentrum Stiftung des Offentlichen Rechts, Heidelberg, Germany

[21] Appl. No.: 982,743

[22] PCT Filed: Jun. 7, 1992

[86] PCT No.: PCT/EP92/01524

§ 371 Date: May 10, 1993

§ 102(e) Date: May 10, 1993

[87] PCT Pub. No.: WO93/01288

PCT Pub. Date: Jan. 21, 1993

[30] Foreign Application Priority Data

Jul. 8, 1991 [DE] Germany ............... 41 22 599.6

[51] Int. Cl.⁶ .......... G01N 33/53; C12N 15/64; C12N 15/70
[52] U.S. Cl. ............ 435/7.1; 435/172.3; 435/320.1
[58] Field of Search ............... 435/320.1, 172.3, 435/6, 7.1; 536/23.53

[56] References Cited

FOREIGN PATENT DOCUMENTS 9209690  6/1992  WIPO .

OTHER PUBLICATIONS

Muller, H., Ph.D. thesis, Univ. of Heidelberg, cover sheets and pp. 56–58 (1989).
McCafferty et al, Nature 348, pp. 552–554 (1990).
Ward et al, Nature 341, pp. 544–546 (1989).
Cwirla et al, Proc. Natl. Acad. Sci. USA 87, pp. 6378–6382 (1990).
Scott et al, Science 249, pp. 386–390 (1990).
Breitling et al, Gene 104, pp. 147–153 (1991).
Huse et al, Science 246, pp. 1275–1281 (1989).
Day et al, Ann. Rev. Biophys. Biophys. Chem. 17, pp. 509–539 (1988).
Smith et al, Science 228, pp. 1315–1317 (1985).
Parmley et al, Gene 73, pp. 305–318 (1988).
Devlin et al, Science 249, pp. 404–406 (1990).
Amit et al, Science 233, pp. 747–753 (1986).
Verhoeyen et al, Science 239, pp. 1534–1536 (1988).
Breitling et al, J. Mol. Biol. 189, pp. 367–370 (1986).
Bass et al, Proteins: Structure, Function and Genetics, vol. 8, No. 4 1990, Wiley Press, NY, US; pp. 309–314.
Bujard et al, Methods Enzymol. 155, pp. 416–433 (1987).
Lanzer et al. Proc. Natl. Acad. Sci. USA 85, pp. 8973–8977 (1988).
Goldsmith et al, Biochemistry 16, pp. 2686–2694 (1977).
Boeke et al, Proc. Natl. Acad. Sci. USA 79, pp. 5200–5204 (1982).
Crissman et al, Virology 132, pp. 445–455 (1984).
Davis et al, J. Mol. Biol. 181, pp. 111–121 (1985).
Pluckthun et al, J. Biol. Chem. 262, 3951–3957 (1987).
Laemmli et al, Nature 227, pp. 680–685 (1970).
Towbin et al, Proc. Natl. Acad. Sci. USA 76, pp. 4350–4354 (1979).
Webster et al., Structure and Assembly of the Class I Filamentous Bacteriophage, Duke University Medical Center pp. 236–267 (1985).
Sambrook et al, "Molecular Cloning", 1989, pp. 4.17–4.19 and 17.29–17.30.

*Primary Examiner*—George G. Elliott
*Assistant Examiner*—Terry A. McKelvey
*Attorney, Agent, or Firm*—Birch, Stewart, Kolasch & Birch, LLP

[57] ABSTRACT

A phagemid has been constructed that expresses an antibody fused to coliphage pIII protein. The phagemid is suitable for selecting specific antibodies from large gene libraries with small quantities of antigen. The antibody-pIII gene can be strongly repressed, so that it allows antibody libraries to be amplified without the danger of deletion mutants predominating. After induction, large quantities of the fusion protein may be expressed.

7 Claims, 4 Drawing Sheets

FIG. 1B

RBS → pelB leader
                    MetLysTyrLeuLeuProThrAlaAlaAlaGlyLeuLeu
86
<u>GAATTC</u>ATTAAAGAGGAGAAATTAACTCCATGAAATACCTTGCTGCCAGCCGGCCTGGCTTG
EcoRI                       (NcoI)

→ VH                                    523—tag-linker
151                                            SerSerGluGluGly
LeuLeuLeuAlaAlaAlaGlnProAlaMetAlaGlnValGlnLeuGln...SerSerGluGluGly
CTGCTGCTGGCAGCTGCAGCCGGGGCGATGGCGCAAGTTCAGCTGCAG...TCCTCAGAGAAGGT
                                         PstI → VL  895
                                              LysArgThr
538                                            
GluPheSerGluAlaArgGluAspMetAlaAlaAlaLeuGluLysGlyAspIle...LysArgThr
<u>GAATTC</u>TCAGAGGCTCGTGAAGATATGGCTGCACTTGAGAAAGGTGATATC...AAACGTACG
EcoRI                                         EcoRV → M13 gene III
904
ValAlaAlaProGlySerLysAspIleArgAlaGluThrValGluSerCys...
GTAGCAGCTCCTGGATCCAAAGATATCAGAGCTGAAACTGTTGAAAGTTGT...
       BamHI      EcoRV       forward primer 2137
...ArgAsnLysGluSerStopStop
...CGTAATAAGGAGTCTTAATGACTCTAGAGTCAGCTT
             <u>TTATTCCTCAGAATTACT</u>CTAGA (HindIII)
             backward primer

PHAGEMID FOR ANTIBODY SCREENING

This application is a 371 of PCT/EP92/01524, filed Jul. 6, 1992.

The present invention concerns phagemids for the selection of specific antibodies from large recombinant libraries, the production of these phagemids and their use to select specific antibodies from large recombinant libraries using small amounts of antigen.

Plasmid and phage antibody libraries have been established in E. coli from PCR amplified immunoglobulin families following immunization. Recombinant antibodies to immunogens were selected by an ELISA assay of the bacterial supernatant from isolated bacterial colonies (Ward, E. S., Güssow, D., Griffiths, A. D., Jones, P. T. & Winter, G.: Binding activities of a repertoire of single immunoglobulin variable domains secreted from Escherichia coli. Nature 341 (1989) 544–546) or by screening nitrocellulose plaque lift-offs of bacterial colonies for reactivity to the radioactively labeled immunogen (Huse, W. D., Sastry, L., Iverson, S. A., Kang, A. S., Alting-Mees, M., Burton, D. R., Benkovic, S. J. and Lerner, R. A.: Generation of a large combinatorial library of the immunoglobin repertoire in phage lambda. Science 246 (1989) 1275–1281). However, for the selection of specific antibodies from randomly combined light and heavy chain libraries of non-immunized animals that do not contain a preponderance of antibodies to a particular antigen, a procedure is required for screening millions of antibody producing bacteria.

A possible way to screen a broad range of antibodies is to attach recombinant antibodies to the surface of bacteria or bacteriophages so that they can then be rapidly selected by antigens bound to a solid phase. Given the difficulties of targeting proteins to the cell surface of bacteria, an attractive candidate in view of its small size and relatively simple genetic make-up is the M13 family of filamentous bacteriophages (for reviews see Webster, R. E. and Lopez, J. in "Virus Structure and Assembly" ed. S. Casjens, publ. Jones and Bartlett Inc., Boston/Portala Valley, USA, 1985; Day, L. A., Marzec, C. J., Reisberg, S. A. and Casadevall, A.: DNA packaging in filamentous bacteriophages. Ann. Rev. Biophys. Biophys. Chem. 17 (1988) 509–539).

The product of gene III (pIII) is a relatively flexible and accessible molecule composed of two functional domains; an amino-terminal domain that binds to the F pilus of male bacteria during infection and a carboxy-terminal domain buried within the virion that is important for morphogenesis. Peptides can be inserted between the two domains of pIII (Smith, G. P.: Filamentous fusion phage: novel expression vectors that display cloned antigens on the virion surface. Science 228 (1985) 1315–1317) or near the N-terminus (Parmley, S. F. and Smith, G. P.: Antibody-selectable filamentous fd phage vectors: affinity purification of target genes. Gene, 73 (1988) 305–318) without destroying its functions in morphogenesis and infection. After much pioneering work on the use of pIII in fd phages for carrying foreign peptides, Parmely and Smith (1988, a.a.O.) showed that peptide epitopes inserted at the aminoterminal end could bind phages to immobilized antibodies. As a consequence of this work it has been possible to generate peptide libraries that can be screened for binding to ligands and antibodies (Scott, J. K. and Smith, G. P.: Searching for peptide ligands with an epitope library. Science 249 (1990) 386–390; Devlin, J. J., Panganiban, L. C. and Devlin, P. E.: Random peptide libraries: A source of specific protein binding molecules. Science 249 (1990) 404–406; Cwirla, S. E., Peters. E. A., Barrett, R. W. and Dower, W. J. Peptides on phage, a vast library of peptides for identifying ligands.: Proc. Natl. Acad. Sci. USA, 87 (1990) 6378–6382).

McCafferty, J., Griffiths, A. D., Winter, G. and Chiswell, D. J.: Phage antibodies: filamentous phage displaying antibody variable domains. Nature, 348 (1990) 552–554 reported the assembly of an antibody-pIII fusion protein into an fd phage with a $Tet^R$ gene after inserting antibody DNA into the 5' end of gene III. The phage remained infectious and was able to be enriched by affinity chromatography. However, fusion phage have been shown to be mainly useful for displaying relatively small inserts, probably, because the large inserts have an adverse effect on the infectivity function of pIII (Parmlee and Smith, 1988, a.a.O). There is a large risk, therefore, that phage libraries will quickly become dominated by deletion mutants after library amplification.

Thus the technical problem underlying the present invention is to provide a more efficient mean for screening antibody libraries in bacteria.

This problem is solved by providing a phagemid according to claim 1 that expresses a functional antibody-pIII fusion protein. Preferably the antibody is a single-chain antibody. DNA coding for an antibody-pIII fusion protein, preferably a single-chain antibody-pIII fusion protein, was incorporated into a phagemid. A major advantage of the phagemid system of this invention over McCafferty et al. (see above) is that it can be propagated as a plasmid and is not under any selection pressure to remove antibody DNA, since the expression of the fusion protein is tightly repressed. This is particularly important during the amplification of antibody libraries when faster proliferating deletion mutants could quickly dominate. The phagemid DNA, being less than half the size of the above phage DNA, also transform bacteria more efficiently. Moreover, in contrast to the above mentioned phage system, large quantities of the smaller phagemid DNA are produced and large amounts of antibody protein are available after induction, thereby greatly facilitating its analysis. Expression of the antibody-pIII fusion protein, preferably the single-chain antibody-pIII fusion protein, using the pSEX phagemid (see below) and its packaging into viral particles greatly facilitate the establishment of bacterial systems for the isolation of high affinity antibodies. Millions of antibody-producing clones from antibody libraries can now be rapidly screened by binding to immobilized antigen. A further advantage over conventional screening methods is that only small amounts of antigen are required, an important factor when the supply of a rare protein is limited. This system also offers the possibility of screening randomly mutated antibodies in order to increase their binding affinities. The procedure could be repeated many times until the desired specificity is achieved. It is now feasible for the first time to carry out large scale differential screening analyses of related cells and organisms. A substractive selection, e.g., using normal and neoplastic cells could be used to identify tumor associated antigens. The phagemid system also proves to be extremely useful for investigating the component of molecular interactions e.g. by selecting antibodies that inhibit ligand receptor binding.

Furthermore, the system of this invention is mostly useful for presenting other proteins or peptides at the surfaces of phagemid viral particles. For this purpose the DNA encoding the antibody has to be replaced with DNA of the desired polypeptide.

BRIEF DESCRIPTION OF THE DRAWINGS

FIG. 1(b) (SEQ ID NOS:7–15) describes the ribosome binding site (RBS), leader sequence of pectate lyase, tag-linker and the PCR primers for pIII.

DETAILED DESCRIPTION OF THE INVENTION

The following Examples illustrate but not restrict the present invention.

EXAMPLES

Example 1
Construction of phagemid (pSEX)

Figures 1A, 1C:
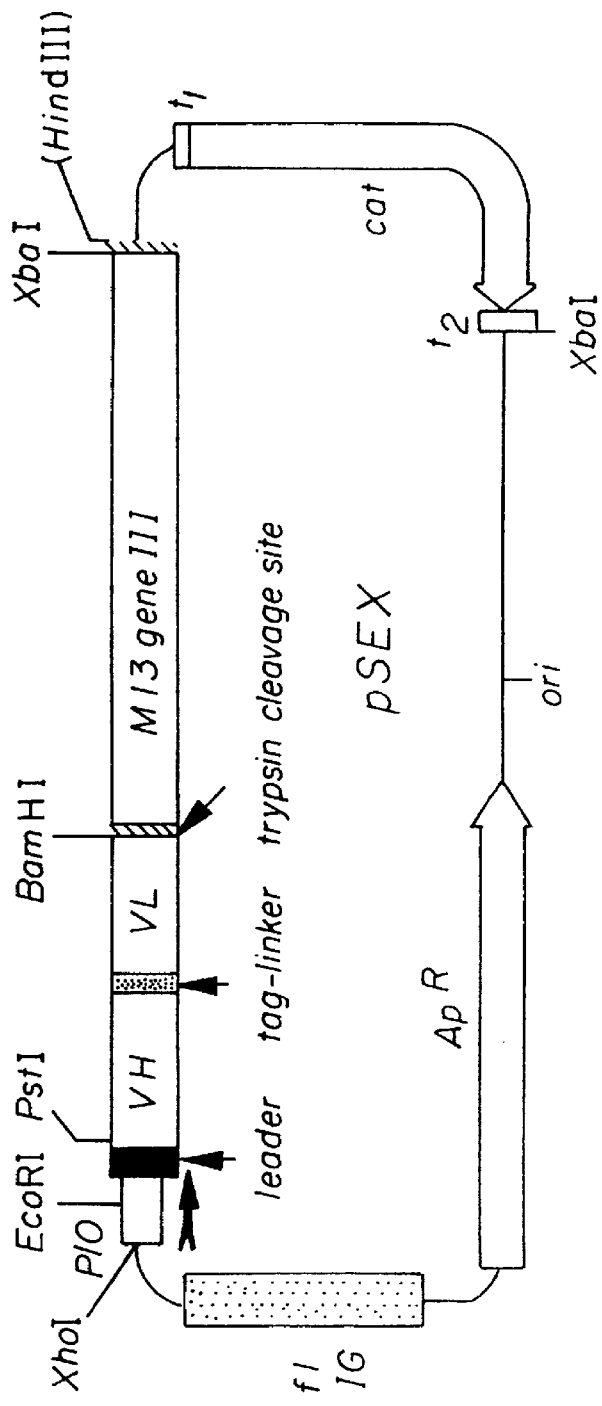
FIG. 1(a) is a restriction map of the phagemid pSEX.
FIG. 1(c) (SEQ ID NOS:16–17) describes an alternative tag-linker sequence.

DNA coding for a single chain antibody (scAb) and pIII were cloned into pUC119 after insertion of a specific set of restriction sites and a protease sensitive joining sequence into the multiple cloning site. The Ab-DNA coded for the heavy and light chain variable domains of a humanised Ab against hen egg white lysozyme derived from the anti-lysozyme Ab D1.3 (Amit et al., Science 233, p. 747–754, 1986; Verhoeyen, M. et al. Science 239 p. 1534–1536, 1988). These domains were joined by an eighteen amino acid linker sequence containing the epitope for the monoclonal Ab YOL1/34 (Breitling, F. and Little, M.: Carboxy-terminal regions on the surface of tubulin and microtubules. Epitope locations of YOL1/34, DM1A and DM1B. J. Mol. Biol. 189 (1986), 367–370), thus enabling the Ab to be identified. To provide a more flexible junction to pIII, the 3'end of the light chain DNA was modified by the addition of nucleotides coding for the first six amino acids of the human kappa constant domain followed by a BamHI restriction site. pIII DNA was amplified from the bacteriophage M13 using primers corresponding to the 5' and 3' ends of gene III. The Ab-pIII-DNA was then cloned into a phagemid of the pDS family that contains a coliphage T7 promoter combined with two lac operators (Bujard, H., Gentz, R., Lancer, M., Stüber, D., Müller, H.-M., Ibrahim, I., Häuptle, M.-T. and Dobberstein, B.: A T5 promoter-based transcription-translation system for the analysis of proteins in vitro and in vivo. Methods Enzymol. 155 (1987) 416–433; Lancer, M. and Bujard, H.: Promoters determine the efficiency of repressor action. Proc. Natl. Acad. Sci. USA 85 (1988) 8973–8977); Müller, H.-M. Ph.D. thesis, Univ. of Heidelberg, 1989). In a final step, DNA coding for the leader sequence of the bacterial enzyme pectate lyase was ligated to the 5' end of the Ab-DNA resulting in the phagemid pSEX (FIG. 1a). The leader, linker and PCR primer sequences are shown in FIG. 1b. An alternative linker sequence (FIG. 1c) with the YOL1/34 epitope placed at the end of the linker containing a useful restriction site for the insertion of Ab libraries was also employed. Although both of these tag-linkers contain a significant number of acidic residues, they appeared to have no effect on the production of functional scAbs when compared to scAbs with linkers composed only of the neutral amino acids glycine and serine.

The plasmid pSex (ATCC designation 97105) was deposited on Mar. 27, 1995 with the depository American Type Tissue Collection, Rockville, Md. 20852 USA.

Example 2
Expression of antibody-pIII fusion protein

Figures 2A, 2B:
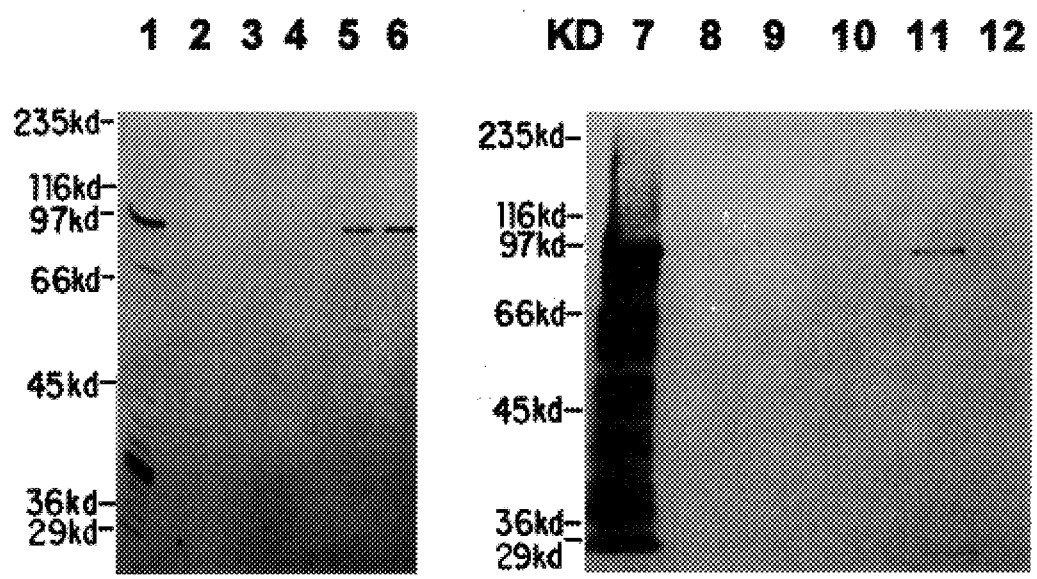
FIG. 2 shows the results of a Western blot analysis for identification of the antibody-pIII fusion protein.

To test whether the completed phagemid vector was able to express the full length fusion protein, 100 $\mu$M IPTG was added to a log phase culture of E. coli transformed with pSEX. The culture showed a marked decline in its rate of growth compared to the control indicating a significant synthesis of phagemid encoded protein. On Western blot analysis, the antibody-pIII construct was identified by three antibodies; a monoclonal antibody to part of the linker sequence (Glu-Glu-Gly-Glu-Phe-Ser-Glu-Ala-Arg) (SEQ ID NO:10/residues 3–11) and two anti-peptide rabbit sera against N-terminal sequences of the heavy and light chains (SEQ ID NO:1) Gln-Val-Gln-Leu-Gln-Gln-Ser-Gly-Gly-Gly (SEQ ID NO:1) and Asp-Ilu-Gln-Met-Thr-Gln-Ser-Pro-Ser-Ser (SEQ ID NO:2), respectively). It migrated with an apparent molecular weight of 93 kd (FIG. 2). The large size of the fusion protein (predicted: Mr 68100) is most probably due to the pIII component (Mr 42100) that migrates with an apparent molecular weight of approximately 55000–70000 kd (Goldsmith, M. E. and Konigsberg, W. H.: Adsorption protein of the bacteriophage fd: isolation, molecular properties and location in the virus. Biochemistry, 16 (1977) 2686–2694). Partial proteolysis of the fusion protein was indicated by the presence of some minor bands of lower molecular weight that were identically stained by all three antibodies.

Cell fractionation showed that the protein was present in the cytoplasmic and membrane fractions but not in the periplasm and culture supernatant (FIG. 2, lanes 3–6) in contrast to the antibody component alone without pIII that was secreted into the periplasm and medium (data not shown). This was not surprising since pIII is assembled onto phage particles from the inner bacterial membrane, a process that appears to be dependent only on the C-terminal domain. Deletion mutants of pIII without this domain pass into the periplasm without becoming attached to the cytoplasmic membrane (Boeke, J. D. and Model, P.: A prokaryotic membrane anchor sequence: carboxyl terminus of bacteriophage f1 gene III protein retained in the membrane. Proc. Natl. Acad. Sci. USA 79 (1982) 5200–5204) and normal phage particles are not assembled (Crissman, J. W. and Smith, G. P.: Gene III protein of filamentous phages: evidence for a carboxy-terminal domain with a role in morphogenesis.: Virology, 132 (1984) 445–455). The anchor sequence is probably a hydrophobic stretch of twenty three amino acids at the carboxy-terminus (Davis, N. G., Boeke, S. and Model, P.: Fine structure of a membrane anchor domain. J. Mol. Biol. 181 (1985) 111–121).

The ability of the fusion protein to bind antigen was investigated by passing the triton soluble fraction over a column of lysozyme bound to sepharose. Western blots of the unbound material and the fractions obtained after thoroughly washing and eluting with 0.05M diethylamine showed that the full length fusion protein was indeed specifically retained on the lysozyme column (FIG. 2, lanes 7–12).

Example 3
Packaging of the pSEX phagemid

Figure 3:
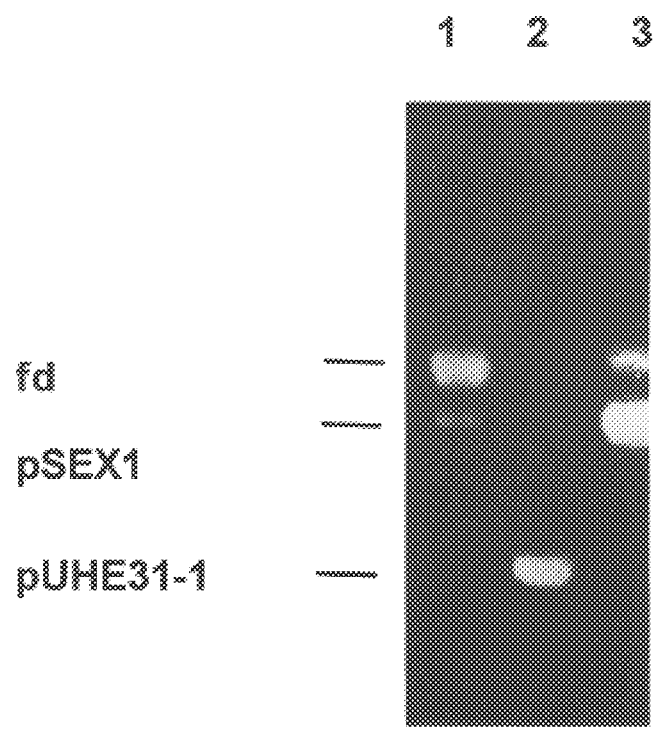
FIG. 3 shows the results of gel electrophoresis of circular single stranded pSEX.

To determine whether the phagemid expression vector could be packaged, E. coli containing pSex were multiply infected with phage fd. IPTG was not added since it was found to have an inhibitory effect on phagemid packaging. A similar finding was recently reported by Bass et al., Proteins 8, S. 309–314 (1990) who constructed a phagemid that expresses a fusion protein of human growth hormone and the C-terminal domain of pIII. Examination of Ab-pIII production with and without IPTG after adding phage fd showed that the phage alone was able to induce expression (FIG. 3). A possible explanation is that one of the phage gene products interferes with the binding of lac repressor to the operator. Alternatively, phage proteins binding to the intergenic region might affect the topology of the phagemid and cause the release of the lac repressor. Whatever the reason, we have found that moving the intergenic region $10^3$ nucleotides to the other side of the bla gene has no effect on this phenomenon (data not shown).

Agarose gel electrophoresis of the DNA from virus particles secreted into the medium showed, in addition to the single stranded DNA of fd, a larger quantity of smaller DNA that was compatible in size with single stranded pSEX. Further proof of phagemid packaging and the production of infectious particles was shown by infecting *E.coli* with the secreted virus particles. $10^{10}$/ml AmpR colonies of *E.coli* were obtained in comparison to $3\times10^9$ pfu.

To determine whether the packaged phagemid had incorporated the antibody-pIII fusion protein, 90 µl culture supernatant containing $5\times10^8$ packaged phagemids determined as $Amp^R$ transducing units was mixed with a 1000-fold excess of wild type fd phage and passed over a column of immobilized lysozyme. After thoroughly washing with ten bed volumes of PBS, 1M NaCl and 0.5M NaCl in 0.1M NaHCO at pH 8.3, respectively, the phagemid particles were eluted with 0.05M diethylamine. The eluate was neutralized with 0.5M $NaH_2PO_4$ and assayed for the number of phages and packaged phagemids (Table). A specific enrichment of up to 121-fold was achieved, thus demonstrating the incorporation of functional antibody-pIII constructs into phagemid particles. The binding properties of the phagemid particles might be further increased by using a pIII deletion mutant for packaging. This would ensure that only those phagemids coding for functional fusion proteins would be packaged and all five pIII proteins on a phagemid particle would be fused to antibodies.

DESCRIPTION OF THE FIGURES

FIGS. 1A–1C Construction of pSex, a phagemid for antibody screening

VH and VL are heavy and light chain variable domains, respectively, of an anti-lysozyme Ab.

FIG. 1A Construction.

To provide the necessary restriction sites, the oligonucleotides 5'GCTGAATTCGGATCCATAGGGC-CCTCTAGAGTCGAC3' (SEQ ID NO:3) and 5'AATTGTCGACTCTAGAGGGCCCTATGGATCCCAA-TTCAGCTGCA3' (SEQ ID NO:4) were 5' phosphorylated, hybridized and ligated to pUC119 that had been cleaved with PstI and EcoRI and dephosphorylated. In an optional step to create a protease sensitive sequence, the hybridized oligonucleotides 5'GATCCAAAGATATCAGAGGGCC3' (SEQ ID NO:5) and 5'CTCTGATATCTTTG3' (SEQ ID.NO:6) were inserted between the BamHI and ApaI sites of the first set of oligonucleotides. scAB-DNA was then inserted between the PstI and BamHI followed by the blunt end ligation of pIII DNA after cleaving the phagemid with ApaI and treating with T4 DNA polymerase to remove 3' overhanging ends. pSEX was constructed by combining the multiple cloning site of pUHE24-2 with the closely related phagemid pDS31-1 that contains an additional f1 intergenic region (Bujard et al., 1987, see above,; Müller, 1989, see above). The pDS31-1 sequence extends from Xho1 anticlockwise to a HindIII site (in parentheses) that was lost after a blunt end ligation. pUHE24-2 is essentially identical to pDS6 (Bujard et al., 1987) with a coliphage T7 promoter combined with two lac operators and a ribosome binding site (PA1/04/03, Lancer and Bujard, 1988, see above; Lanzer, 1988, see above). The resulting phagemid was cleaved with HindIII and the 5' overhanging ends were filled up with Klenow fragment. After a further digestion with PstI, the PstI-HincII Ab-pIII-DNA fragment was inserted into the phagemid. In a final step, synthetic DNA coding for the leader sequence of the bacterial enzyme pectate lyase and for the first four amino acids of the heavy chain was inserted between the NcoI and PstI restriction sites. pUHE plasmids were propagated in *E.coli* 71–18 with the plasmid pDM1 that expresses lac repressor, pUC plasmids were propagated DH5α and the antibody-pIII fusion protein was expressed in JM101.

FIG. 1B Sequence of the ribosome binding site (RBS), leader sequence of pectate lyase, tag-linker and the PCR primers for pIII. Underlined amino acids indicate the epitope for YOL1/34. The following amino acids in the linker sequence are a continuation of the α-tubulin sequence. (Note SEQ ID NOS:7–15).

FIG. 1C Alternative tag-linker sequence. Underlined amino acids indicate the epitope for YOL11/34. The preceding linker amino acids are a continuation of Ab sequence into the constant domain. (SEQ ID NOS:16–17).

FIG. 2 Inducibility, cellular localization and antigen binding of the antibody-pIII fusion protein analyzed by gel electrophoresis on 8% polyacrylamide gels and Western blotting Lanes 1 and 2: Total cells after 1 h induction with 100 µM IPTG (1) or without IPTG (2).

Lanes 3–6: Cell fractionation; 3: culture supernatant, 4: periplasmic enriched fraction, 5: soluble cytoplasmic fraction, 6: 1% triton extract.

Lanes 7–12: Lysozyme affinity chromatography of the 1% triton extract from induced and non-induced cells, 7: effluent (+IPTG), 8: effluent (–IPTG), 9: last wash (+IPTG), 10: last wash (–IPTG), 11: eluate (+IPTG), 12: eluate (–IPTG).

Lanes 1–6 were stained using the monoclonal antibody YOL1/34 (Serotec, Oxford, U.K.) and lanes 7–12 using an antiserum to the N-terminal sequence of the light chain.

Method

Antisera to the heavy and light chains were obtained by the subcutaneous injection of rabbits with the amino-terminal peptides Gln-Val-Gln-Leu-Gln-Gln-Ser-Gly-Gly-Gly(AC) (SEQ ID NO:1) and Asp-Ilu-Gln-Met-Thr-Gln-Ser-Pro-Ser-Ser(AC) (SEQ ID NO:2) respectively, coupled to keyhole limpet heamocyanin. To investigate the expression of the fusion protein, the pelleted bacteria of IPTG-induced cultures were resuspended in 30 mM Tris/HCl, pH 8.0 containing 20% sucrose. 1 mM EDTA, 1 mg/ml chick lysozyme and incubated for 10 min on ice. After centrifuging for 1 min at 15000 g, the supernatant containing the periplasmic proteins was collected and the pellet was sonicated in 0.1M Tris/HCl pH 8.0. The soluble cytosolic fraction was decanted after centrifuging for 5 min at 15000 g and the resuspended pellet was incubated in 1% Triton X100 to obtain the membrane bound fraction. All the fractions were analyzed for β-lactamase activity according to Pl ückthun, A. and Knowles, J. R.: The consequences of stepwise deletions from the signal-processing site for β-lactamase. J. Biol. Chem. 262 (1987) 3951–3957 to check the efficiency of the fractionation procedure. The triton soluble fraction was diluted a 100-fold with PBS before applying to affinity columns. For affinity chromatography, chick lysozyme (Boehringer, Mannheim, FRG) was coupled to cyanogen bromide activated Sepharose (Pharmacia) according to the instructions of the manufacturer. The lysozyme-Sepharose was incubated for 20 min at room temperature with the extracts and poured into columns that were subsequently washed with ten bed volumes of PBS, 1M NaCl and 0.5M NaCl in 0.1M NaHCO$_3$ at pH 8.3, respectively, before eluting with 0.05M diethylamine. All the fractions were precipitated with trichloracetic acid (final concentration 20%) and resolved on SDS polyacrylamide gels (Laemmli, U.K.: Cleavage of structural proteins during the assembly of the head of the bacteriophage T4. Nature 227 (1970) 680–685). Western blots were performed according to Towbin, H. Staehelin, T. and Gordon, I.: Electrophoretic transfer of protein from polyacrylamide gels to nitro-cellulose sheets: procedures and some applications (1979), Proc. Natl. Acad. Sci. USA 76, 4350–4354, using second antibodies coupled to horseradish peroxidase with diaminobenzidene as substrate.

FIG. 3 Gel electrophoresis of circular single stranded pSEX

Lane 1: fd, lane 2: control phagemid pUHE31-1 with fd, lane 3: pSEX1 with fd.

DNA from fd virions and packaged phagemid particles was applied to 0.8% agarose gels in 1×TBE according to Sambrook, J., Fritsch, E. F. and Maniatis, T. in Molecular Cloning: A Laboratory Manual, 2nd. ed. Cold Spring Harbor Laboratory (1989) and stained with ethidium bromide.

Method

For the preparation of packaged phagemids, *E. coli* JM101 containing pSEX1 was plated onto M9 minimal medium and incubated for 30 h at 37° C. 2 ml of the same medium was inoculated with one of the colonies and incubated at 37° C. with vigorous aeration until it reached an optical density of about 0.2 at 600 nm. 0.5 ml of LB medium and a 10-fold excess of phage fd were then added to the culture and it was incubated for a further 3 h at 37° C. After carefully centrifuging twice at 15000 g for 5 min at room temperature, the supernatant was adjusted to a final concentration of 4% polyethylene glycol (Serva PEG 6000) and 0.5M NaCl and left to stand overnight at 4° C. The phagemids were sedimented by centrifuging at 15000 g for 20 min at room temperature and suspended in 200 μl of a Tris-EDTA buffer, pH 7.5. Phagemid DNA was prepared by shaking with one volume of phenol for ten minutes followed by treatment with chloroform-isopropanol and precipitated with isopropanol (Sambrook, J., Fritsch, E. F. and Maniatis, T. in Molecular Cloning: A Laboratory Manual, 2nd. ed. Cold Spring Harbor Laboratory (1989)).

TABLE

Specific enrichment of packaged phagemids on an antigen affinity colum

| | Total Volume (ml) | Amp$^r$ Colonies | | | Total pfu | | | Excesss pfu/Amp$^r$ | Enrichment Factor |
|---|---|---|---|---|---|---|---|---|---|
| | | Plated Volume (μl) | Number | Total | Plated Volume (μl) | Number | Total | | |
| Applied | 10 | $10^{-3}$ | 51 | $5.1 \times 10^8$ | $10^{-6}$ | 45 | $4.5 \times 10^{11}$ | 882 | — |
| Eluted | 1.1 | $10^{-1}$ | 26 | $2.9 \times 10^5$ | $10^{-2}$ | 19 | $2.1 \times 10^6$ | 7.3 | 121 |

We claim:

1. A phagemid comprising a DNA encoding a single-chain antibody-coliphage pIII fusion protein, wherein the fusion protein contains a contiguous full length coliphage pIII protein.

2. The phagemid according to claim 1, wherein the fusion protein contains a protease-sensitive region between the antibody and the coliphage pIII protein.

3. The phagemid according to either claim 1 or claim 2, wherein the phagemid comprises the genetic elements and DNA sequences (SEQ ID NOS:7–17) of FIGS. 1(a)–1(c).

4. A process of producing the phagemid according to claim 1, comprising fusing a DNA encoding the single-chain antibody to a DNA encoding the contiguous full length coliphage pIII protein and inserting the resulting DNA into a phagemid vector.

5. The process according to claim 4, further comprising inserting a DNA encoding a protease-sensitive region between the DNA encoding the single-chain antibody and the DNA encoding the coliphage pIII protein.

6. A method of selecting antibodies from an antibody library, comprising screening said antibody library with an antigen, wherein said antibody library consists of phagemids according to either claim 1 or claim 2.

7. A method of presenting a peptide or protein at the surface of a phagemid viral particle, comprising producing said phagemid viral particle, wherein said phagemid viral particle comprises a DNA sequence encoding said peptide or protein fused to a DNA sequence encoding a contiguous full length coliphage pIII protein.

* * * * *

UNITED STATES PATENT AND TRADEMARK OFFICE
CERTIFICATE OF CORRECTION

PATENT NO. : 5,849,500
DATED : Dec. 15, 1998
INVENTOR(S) : BREITLING et al.

It is certified that error appears in the above-identified patent and that said Letters Patent is hereby corrected as shown below:

On the title page:

Item "[75] Inventors:", please correct the assignee's name from "Deutsches Krebsforschungszentrum Stiftung des Offenlichen Rechts" to -- Deutsches Krebsforschungszentrum Stiftung des öffenlichen Rechts --.

Item "[22] PCT Filed:", please change "Jun. 7, 1992" to --July 6, 1992 --.

Signed and Sealed this

Sixteenth Day of May, 2000

Attest:

Q. TODD DICKINSON

*Attesting Officer*     *Director of Patents and Trademarks*

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: N-terminal ( i x ) FEATURE:
        ( A ) NAME/KEY: Peptide
        ( B ) LOCATION: 1..10
        ( D ) OTHER INFORMATION: /label=peptide
            / note= "N-terminal sequence of heavy chain variable domain of scAb to hen egg white lysozyme."

( x i ) SEQUENCE DESCRIPTION: SEQ ID NO:1:

Gln Val Gln Leu Gln Gln Ser Gly Gly Gly
        1                5                              10

(2) INFORMATION FOR SEQ ID NO:2:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (v) FRAGMENT TYPE: N-terminal (ix) FEATURE:
        (A) NAME/KEY: Peptide
        (B) LOCATION: 1..10
        (D) OTHER INFORMATION: /label=peptide
            / note= "N-terminal sequence of light chain
            variable region of scAb to hen egg white lysozyme"

(xi) SEQUENCE DESCRIPTION: SEQ ID NO:2:

Asp Ile Gln Met Thr Gln Ser Pro Ser Ser
1               5                   10

(2) INFORMATION FOR SEQ ID NO:3:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (iii) HYPOTHETICAL: NO (ix) FEATURE:
        (A) NAME/KEY: -
        (B) LOCATION: 1..36
        (D) OTHER INFORMATION: /label=linker top strand (xi) SEQUENCE DESCRIPTION: SEQ ID NO:3:

GCTGAATTCG GATCCATAGG GCCCTCTAGA GTCGAC    36

(2) INFORMATION FOR SEQ ID NO:4:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..44
        (D) OTHER INFORMATION: /label=linker bottom strand (xi) SEQUENCE DESCRIPTION: SEQ ID NO:4:

AATTGTCGAC TCTAGAGGGC CCTATGGATC CGAATTCAGC TGCA    44

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..22
        (D) OTHER INFORMATION: /label=linker / note= "top strand of linker encoding a
            protease- sensitive
            sequence"

( x i ) SEQUENCE DESCRIPTION: SEQ ID NO:5:

GATCCAAAGA TATCAGAGGG CC                                                                                  22

( 2 ) INFORMATION FOR SEQ ID NO:6:

( i ) SEQUENCE CHARACTERISTICS:
            ( A ) LENGTH: 14 base pairs
            ( B ) TYPE: nucleic acid
            ( C ) STRANDEDNESS: single
            ( D ) TOPOLOGY: linear ( i i ) MOLECULE TYPE: DNA ( i x ) FEATURE:
            ( A ) NAME/KEY: -
            ( B ) LOCATION: 1..14
            ( D ) OTHER INFORMATION: /label=linker
                    / note= "bottom strand of linker encoding
                    protease- sensitive sequence"

( x i ) SEQUENCE DESCRIPTION: SEQ ID NO:6:

CTCTGATATC TTTG                                                                                           14

( 2 ) INFORMATION FOR SEQ ID NO:7:

( i ) SEQUENCE CHARACTERISTICS:
            ( A ) LENGTH: 110 base pairs
            ( B ) TYPE: nucleic acid
            ( C ) STRANDEDNESS: both
            ( D ) TOPOLOGY: linear ( i i ) MOLECULE TYPE: DNA ( i x ) FEATURE:
            ( A ) NAME/KEY: -
            ( B ) LOCATION: 1..110
            ( D ) OTHER INFORMATION: /label=fragment
                    / note= "EcoRI - PstI fragment of pSEX (nucleotides
                    86 - 196), see Fig. 1"

( i x ) FEATURE:
            ( A ) NAME/KEY: CDS
            ( B ) LOCATION: 30..110
            ( D ) OTHER INFORMATION: /product="pelB leader sequence"

( x i ) SEQUENCE DESCRIPTION: SEQ ID NO:7:

GAATTCATTA AAGAGGAGAA ATTAACTCC ATG AAA TAC CTC TTG CCT ACG GCA        53
                                  Met Lys Tyr Leu Leu Pro Thr Ala
                                   1                   5

GCC GCT GGC TTG CTG CTG CTG GCA GCT CAG CCG GCG ATG GCG CAA GTT      101
Ala Ala Gly Leu Leu Leu Leu Ala Ala Gln Pro Ala Met Ala Gln Val
        10              15                  20

CAG CTG CAG                                                          110
Gln Leu Gln
 25

( 2 ) INFORMATION FOR SEQ ID NO:8:

( i ) SEQUENCE CHARACTERISTICS:
            ( A ) LENGTH: 27 amino acids
            ( B ) TYPE: amino acid
            ( D ) TOPOLOGY: linear ( i i ) MOLECULE TYPE: protein ( x i ) SEQUENCE DESCRIPTION: SEQ ID NO:8:

Met Lys Tyr Leu Leu Pro Thr Ala Ala Ala Gly Leu Leu Leu Leu Ala

|   |   |   |   | 1 |   |   |   | 5 |   |   |   |   | 10 |   |   |   |   | 15 |
|---|---|---|---|---|---|---|---|---|---|---|---|---|---|---|---|---|---|---|
| Ala | Gln | Pro | Ala | Met | Ala | Gln | Val | Gln | Leu | Gln |
|   |   |   |   | 20 |   |   |   | 25 |

(2) INFORMATION FOR SEQ ID NO:9:

(i) SEQUENCE CHARACTERISTICS:
        (A) LENGTH: 66 base pairs
        (B) TYPE: nucleic acid
        (C) STRANDEDNESS: both
        (D) TOPOLOGY: linear (ii) MOLECULE TYPE: DNA (ix) FEATURE:
        (A) NAME/KEY: -
        (B) LOCATION: 1..66
        (D) OTHER INFORMATION: /label=fragment
        / note= "tag-linker/scAb boundary in plasmid pSEX
        (nucleotides 523 - 589), see Fig. 1"

(ix) FEATURE:
        (A) NAME/KEY: CDS
        (B) LOCATION: 1..66

(xi) SEQUENCE DESCRIPTION: SEQ ID NO:9:

| TCC | TCA | GAA | GAA | GGT | GAA | TTC | TCA | GAA | GCT | CGT | GAA | GAT | ATG | GCT | GCA | 48 |
|-----|-----|-----|-----|-----|-----|-----|-----|-----|-----|-----|-----|-----|-----|-----|-----|-----|
| Ser | Ser | Glu | Glu | Gly | Glu | Phe | Ser | Glu | Ala | Arg | Glu | Asp | Met | Ala | Ala |   |
| 1   |     |     |     | 5   |     |     |     |     | 10  |     |     |     |     | 15  |     |   |

| CTT | GAG | AAA | GGT | GAT | ATC | 66 |
|-----|-----|-----|-----|-----|-----|----|
| Leu | Glu | Lys | Gly | Asp | Ile |    |
|     |     |     | 20  |     |     |    |

(2) INFORMATION FOR SEQ ID NO:10:

(i) SEQUENCE CHARACTERISTICS:
        (A) LENGTH: 22 amino acids
        (B) TYPE: amino acid
        (D) TOPOLOGY: linear (ii) MOLECULE TYPE: protein (xi) SEQUENCE DESCRIPTION: SEQ ID NO:10:

| Ser | Ser | Glu | Glu | Gly | Glu | Phe | Ser | Glu | Ala | Arg | Glu | Asp | Met | Ala | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Leu | Glu | Lys | Gly | Asp | Ile |
|-----|-----|-----|-----|-----|-----|
|     |     |     | 20  |     |     |

(2) INFORMATION FOR SEQ ID NO:11:

(i) SEQUENCE CHARACTERISTICS:
        (A) LENGTH: 60 base pairs
        (B) TYPE: nucleic acid
        (C) STRANDEDNESS: both
        (D) TOPOLOGY: linear (ii) MOLECULE TYPE: DNA (ix) FEATURE:
        (A) NAME/KEY: -
        (B) LOCATION: 1..60
        (D) OTHER INFORMATION: /label=fragment
        / note= "portion of pSEX plasmid (nucleotides 895-
        954) at scAb/gene III boundary, see Fig. 1"

(ix) FEATURE:
        (A) NAME/KEY: CDS
        (B) LOCATION: 1..60

(xi) SEQUENCE DESCRIPTION: SEQ ID NO:11:

| AAA | CGT | ACG | GTA | GCA | GCT | CCT | GGA | TCC | AAA | GAT | ATC | AGA | GCT | GAA | ACT | 48 |
|-----|-----|-----|-----|-----|-----|-----|-----|-----|-----|-----|-----|-----|-----|-----|-----|-----|

```
Lys  Arg  Thr  Val  Ala  Ala  Pro  Gly  Ser  Lys  Asp  Ile  Arg  Ala  Glu  Thr
 1              5                        10                       15

GTT  GAA  AGT  TGT                                                                    60
Val  Glu  Ser  Cys
               20
```

(2) INFORMATION FOR SEQ ID NO:12:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO:12:

```
Lys  Arg  Thr  Val  Ala  Ala  Pro  Gly  Ser  Lys  Asp  Ile  Arg  Ala  Glu  Thr
 1              5                        10                       15
Val  Glu  Ser  Cys
               20
```

(2) INFORMATION FOR SEQ ID NO:13:

(i) SEQUENCE CHARACTERISTICS:
        (A) LENGTH: 36 base pairs
        (B) TYPE: nucleic acid
        (C) STRANDEDNESS: both
        (D) TOPOLOGY: linear (ii) MOLECULE TYPE: DNA (ix) FEATURE:
        (A) NAME/KEY: -
        (B) LOCATION: 1..36
        (D) OTHER INFORMATION: /label=fragment
        / note= "end of fusion protein-encoding insert in
        pSEX (nucleotides 2137 to HindIII site), see Fig.
        1"

(ix) FEATURE:
        (A) NAME/KEY: CDS
        (B) LOCATION: 1..15
        (D) OTHER INFORMATION: /product="end of gene III portion
        of scAb/gene III fusion protein"

(xi) SEQUENCE DESCRIPTION: SEQ ID NO:13:

```
CGT  AAT  AAG  GAG  TCT  TAATGACTCT AGAGTCAGCT T                                      36
Arg  Asn  Lys  Glu  Ser
 1              5
```

(2) INFORMATION FOR SEQ ID NO:14:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:14:

```
Arg  Asn  Lys  Glu  Ser
 1              5
```

(2) INFORMATION FOR SEQ ID NO:15:

(i) SEQUENCE CHARACTERISTICS:
        (A) LENGTH: 18 base pairs
        (B) TYPE: nucleic acid
        (C) STRANDEDNESS: single
        (D) TOPOLOGY: linear -continued (  i  i  ) MOLECULE TYPE: DNA (  i  x  ) FEATURE:
                    ( A ) NAME/KEY: -
                    ( B ) LOCATION: 1..18
                    ( D ) OTHER INFORMATION: /label=primer
                                / note= "backward primer, see Fig. 1"

(  x  i  ) SEQUENCE DESCRIPTION: SEQ ID NO:15:

TCATTAAGAC TCCTTATT                                                                                            18

( 2 ) INFORMATION FOR SEQ ID NO:16:

(  i  ) SEQUENCE CHARACTERISTICS:
                    ( A ) LENGTH: 63 base pairs
                    ( B ) TYPE: nucleic acid
                    ( C ) STRANDEDNESS: both
                    ( D ) TOPOLOGY: linear (  i  i  ) MOLECULE TYPE: DNA (  i  x  ) FEATURE:
                    ( A ) NAME/KEY: -
                    ( B ) LOCATION: 1..63
                    ( D ) OTHER INFORMATION: /label=linker
                                / note= "alternative tag-linker sequence, see Fig. 1(c)"

(  i  x  ) FEATURE:
                    ( A ) NAME/KEY: CDS
                    ( B ) LOCATION: 1..63

(  x  i  ) SEQUENCE DESCRIPTION: SEQ ID NO:16:

| TCA | GGG | AGT | GCA | TCC | GCC | CCA | AAG | CTT | GAA | GAA | GGT | GAA | TTC | TCA | GAA | 48 |
| Ser | Gly | Ser | Ala | Ser | Ala | Pro | Lys | Leu | Glu | Glu | Gly | Glu | Phe | Ser | Glu |  |
|  1  |     |     |     |  5  |     |     |     |     | 10  |     |     |     |     | 15  |     |    |

| GCG | CGC | GAA | GAT | ATC | 63 |
| Ala | Arg | Glu | Asp | Ile |    |
|     |     |     | 20  |     |    |

( 2 ) INFORMATION FOR SEQ ID NO:17:

(  i  ) SEQUENCE CHARACTERISTICS:
                    ( A ) LENGTH: 21 amino acids
                    ( B ) TYPE: amino acid
                    ( D ) TOPOLOGY: linear (  i  i  ) MOLECULE TYPE: protein (  x  i  ) SEQUENCE DESCRIPTION: SEQ ID NO:17:

Ser Gly Ser Ala Ser Ala Pro Lys Leu Glu Glu Gly Glu Phe Ser Glu
 1           5                   10                  15

Ala Arg Glu Asp Ile
             20